United States Patent
Orito et al.

(10) Patent No.: US 10,207,017 B2
(45) Date of Patent: Feb. 19, 2019

(54) DEODORIZER

(71) Applicant: Mitsubishi Electric Corporation, Tokyo (JP)

(72) Inventors: Mari Orito, Tokyo (JP); Sota Komae, Tokyo (JP); Junichiro Hoshizaki, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 0 days.

(21) Appl. No.: 14/901,413

(22) PCT Filed: Jul. 22, 2014

(86) PCT No.: PCT/JP2014/069365
§ 371 (c)(1),
(2) Date: Dec. 28, 2015

(87) PCT Pub. No.: WO2015/012278
PCT Pub. Date: Jan. 29, 2015

(65) Prior Publication Data
US 2016/0250370 A1    Sep. 1, 2016

(30) Foreign Application Priority Data

Jul. 25, 2013  (WO) .................. PCT/JP2013/070235

(51) Int. Cl.
*A61L 9/014*  (2006.01)
*A61L 9/03*  (2006.01)
(Continued)

(52) U.S. Cl.
CPC .............. *A61L 9/014* (2013.01); *A61L 9/032* (2013.01); *B01D 53/02* (2013.01); *B01D 53/75* (2013.01);
(Continued)

(58) Field of Classification Search
CPC . A61L 9/014; A61L 9/032; B01J 20/06; B01J 20/18; B01J 23/34; B01D 53/75; B01D 53/8687; B01D 53/02
See application file for complete search history.

(56) References Cited

U.S. PATENT DOCUMENTS

| | | | | |
|---|---|---|---|---|
| 5,236,878 A | * | 8/1993 | Inoue ................. | B01D 53/0454 502/63 |
| 2007/0286786 A1 | * | 12/2007 | Ikoma ...................... | B01J 29/26 423/239.2 |
| 2011/0136656 A1 | | 6/2011 | Nariyuki et al. | |

FOREIGN PATENT DOCUMENTS

| | | | | | |
|---|---|---|---|---|---|
| JP | 04079963 A | * | 3/1992 | ............... | A61L 9/16 |
| JP | 05192535 A | * | 8/1993 | ............. | B01D 53/34 |

(Continued)

OTHER PUBLICATIONS

Japanese Office Action dated Aug. 2, 2016 in the corresponding JP application No. 2015-528296. (Partial English translation attached).
(Continued)

*Primary Examiner* — Regina M Yoo
(74) *Attorney, Agent, or Firm* — Posz Law Group, PLC

(57) ABSTRACT

A deodorizer includes: a body case having an inlet and an outlet opening outward and having an air duct that provides communication between the inlet and the outlet; a blowing fan included in the body case, for introducing indoor air into the air duct extending from the inlet to the outlet; deodorizing means provided in a middle of the air duct, through which the introduced air can pass; heating means placed to face at least a partial region of the deodorizing means, for heating the deodorizing means at 200° C. or less; and a controller for controlling operations of the blowing fan and the heating means. The deodorizing means includes, on a carrier, an adsorbent that does not oxidatively decompose an adsorbed material, a catalyst component that oxidatively (Continued)

decomposes the adsorbed material, and a rate of conversion of alcohol into acetic acid by the catalyst component is 15% or less on average across the entire deodorizing means.

12 Claims, 6 Drawing Sheets

(51) Int. Cl.
    *B01D 53/02* (2006.01)
    *B01J 23/34* (2006.01)
    *B01D 53/75* (2006.01)
    *B01D 53/86* (2006.01)
    *B01J 20/06* (2006.01)
    *B01J 20/18* (2006.01)

(52) U.S. Cl.
    CPC .......... *B01D 53/8687* (2013.01); *B01J 20/06* (2013.01); *B01J 20/18* (2013.01); *B01J 23/34* (2013.01); *A61L 2209/11* (2013.01); *A61L 2209/14* (2013.01); *B01D 2253/1085* (2013.01); *B01D 2253/1124* (2013.01); *B01D 2255/1021* (2013.01); *B01D 2255/2073* (2013.01); *B01D 2257/306* (2013.01); *B01D 2257/406* (2013.01); *B01D 2257/702* (2013.01); *B01D 2257/90* (2013.01); *B01D 2258/06* (2013.01); *B01D 2259/4508* (2013.01)

(56) References Cited

FOREIGN PATENT DOCUMENTS

| | | | |
|---|---|---|---|
| JP | H08-243383 A | 9/1996 | |
| JP | H09-056799 A | 3/1997 | |
| JP | H09-215928 A | 8/1997 | |
| JP | H10-165808 A | 6/1998 | |
| JP | H10-277365 A | 10/1998 | |
| JP | 2001-017822 A | 1/2001 | |
| JP | 2010-240233 A | 10/2010 | |
| JP | 2011-024896 A | 2/2011 | |
| WO | 2010007978 A1 | 1/2010 | |
| WO | WO-2012167280 A1 * | 12/2012 | .............. B01J 23/24 |

OTHER PUBLICATIONS

International preliminary report on patentability dated Jan. 26, 2016 for the PCT application No. PCT/JP2014/069365.

Office Action dated Nov. 12, 2015 in corresponding Taiwanese patent application No. 103125459 (and partial English translation).

International Search Report of the International Searching Authority dated Nov. 11, 2014 for the corresponding International application No. PCT/JP2014/069365 (and English translation).

Japanese Office Action dated Dec. 6, 2016 in the corresponding JP application No. 2015-528296. (Partial English translation attached).

Office Action dated Jan. 9, 2017 issued in corresponding CN patent application No. 201480041876.9 (and partial English translation).

Santiago J.A. Figueroa et al., "XANES study of electronic and structural nature of Mn-sites in manganese oxides with catalytic properties," Catalysis Today, vols. 107-108, pp. 849-855, Oct. 30, 2005.

Office Action dated Aug. 23, 2017 issued in corresponding CN patent application No. 201480041876.9 (and partial English translation).

Office Action dated Nov. 21, 2017 issued in corresponding JP patent application No. 2017-022783 (and English translation).

* cited by examiner

DEODORIZER

CROSS REFERENCE TO RELATED APPLICATIONS

This application is a U.S. national stage application of PCT/JP2014/069365 filed on Jul. 22, 2014, which claims priority to International Application No. PCT/JP2013/070235 filed on Jul. 25, 2013, the contents of which are incorporated herein by reference.

TECHNICAL FIELD

The present invention relates to a deodorizer that removes an odorous component from indoor air sucked into a body to deodorize the indoor air.

BACKGROUND

A conventionally known deodorizer includes: a body case; an air inlet formed in a front surface of the body case; an air outlet formed in a rear part of an upper surface of the body case; a fan provided in the body case, for sucking air from the air inlet and blowing the air to the air outlet; a fan motor for driving the fan; and a dust collection filter provided upstream of the fan, for collecting dust in the sucked air, wherein the deodorizer further includes, near the air outlet, a deodorizing portion formed by adding a catalyst to a surface of an adsorbent for adsorbing an odorous component, and a heating portion for heating to restore a deodorizing function of the deodorizing portion (for example, Patent Literature 1).

In such a deodorizer, the fan is driven to take indoor air from the air inlet into the body case, the dust collection filter removes dust, and then the odorous component in the indoor air having flowed down to the deodorizing portion is adsorbed by the adsorbent in the deodorizing portion, thereby deodorizing the indoor air. Then, the adsorbent in the deodorizing portion having adsorbed an odor is heated by the heating portion to remove the odorous component, thereby restoring the deodorizing function.

PATENT LITERATURE

Patent Literature 1: Japanese Patent Laid-Open No. 2011-24896

However, the deodorizer described in Patent Literature 1 may cause a reaction with a sudden temperature increase when the odorous component adsorbed by the deodorizing portion is heated depending on use environments. To address this, a reduction in adsorbing capacity of the deodorizing portion, or a reduction in heating temperature of the heating portion is conceivable. However, for the former, a reduction in deodorizing performance per unit area of deodorizing means reduces deodorizing performance per unit time of the deodorizing means, and a deodorizing effect is less actually sensed, or an area of the deodorizing means needs to be increased to increase a size of the deodorizer. For the latter, an oxidative decomposition reaction for decomposing an adsorbed odor material into carbon dioxide and water is incompletely suppressed, thus a material produced by the oxidative decomposition reaction has higher odor intensity than the adsorbed material, and this material may be released from blown-out air and provide discomfort to a user.

SUMMARY

The present invention is achieved in view of the above-described problems, and has an object to provide a deodorizer capable of efficiently reducing odors in indoor air, and efficiently restoring a function of deodorizing means for adsorbing odors.

In accomplishing the above object, there is provided a deodorizer comprising: a body case having an inlet and an outlet opening outward, and having an air duct providing communication between the inlet and the outlet; blowing means included in the body case, for introducing indoor air into the air duct extending from the inlet to the outlet; deodorizing means provided in a middle of the air duct, introduced air passing through the deodorizing means; heating means placed to face at least a partial region of the deodorizing means, for heating the deodorizing means at 200° C. or less; and control means for controlling operations of the blowing means and the heating means, the deodorizing means comprising: an adsorbent that does not oxidatively decompose an adsorbed material, a catalyst component that oxidatively decomposes an adsorbed material and a carrier carrying the adsorbent and the catalyst component; in a regenerating operation for heating the deodorizing means using the heating means, a weight percentage of the catalyst component with respect to components carried by the carrier and a heating temperature and a heating time of the heating means in the regenerating operation being set so that a rate of conversion into acetic acid that is a ratio of a molar amount of acetic acid released from the deodorizing means to a molar amount of ethanol having been adsorbed by the catalyst component is 15% or less on average during the regenerating operation.

In accomplishing the above object, there is provided a deodorizer comprising: a body case having an inlet and an outlet opening outward, and having an air duct providing communication between the inlet and the outlet; blowing means included in the body case, for introducing indoor air into the air duct extending from the inlet to the outlet; deodorizing means provided in a middle of the air duct, introduced air passing through the deodorizing means; heating means placed to face at least a partial region of the deodorizing means, for heating the deodorizing means at 200° C. or less; and control means for controlling operations of the blowing means and the heating means, the deodorizing means comprising: an adsorbent that does not oxidatively decompose an adsorbed material, a catalyst component that oxidatively decomposes an adsorbed material and a carrier carrying the adsorbent and the catalyst component; the deodorizing means being configured so that when the deodorizing means adsorbs ethanol and is heated at a heating temperature of 120° C. to 140° C. for one hour, a rate of conversion into acetic acid representing a ratio of a molar amount of acetic acid released from the deodorizing means to a molar amount of ethanol having been adsorbed is 15% or less.

According to the present invention, a deodorizer can be provided capable of efficiently reducing odors in indoor air, and efficiently restoring a function of deodorizing means for adsorbing odors.

BRIEF DESCRIPTION OF DRAWINGS

FIG. 1(a) is a front view, FIG. 1(b) is a plan view, and FIG. 1(c) is a right side view.

FIG. 2(a) is a front view, FIG. 2(b) is a plan view, and FIG. 2(c) is a right side view.

FIG. 5(a) is a perspective view of the deodorizing portion seen from front, and FIG. 5(b) is a perspective view of the deodorizing portion seen from rear.

FIG. 7(a) is a back view, and FIG. 7(b) is a vertical sectional view of the heating means cut along Z-Z in FIG. 7(a).

FIG. 8(a) is a perspective view of the heating means seen from back, and FIG. 8(b) is a perspective view of the heating means seen from front.

DETAILED DESCRIPTION

Embodiment 1

Embodiment 1 of the present invention will be described with reference to the drawings.

Figure 1:
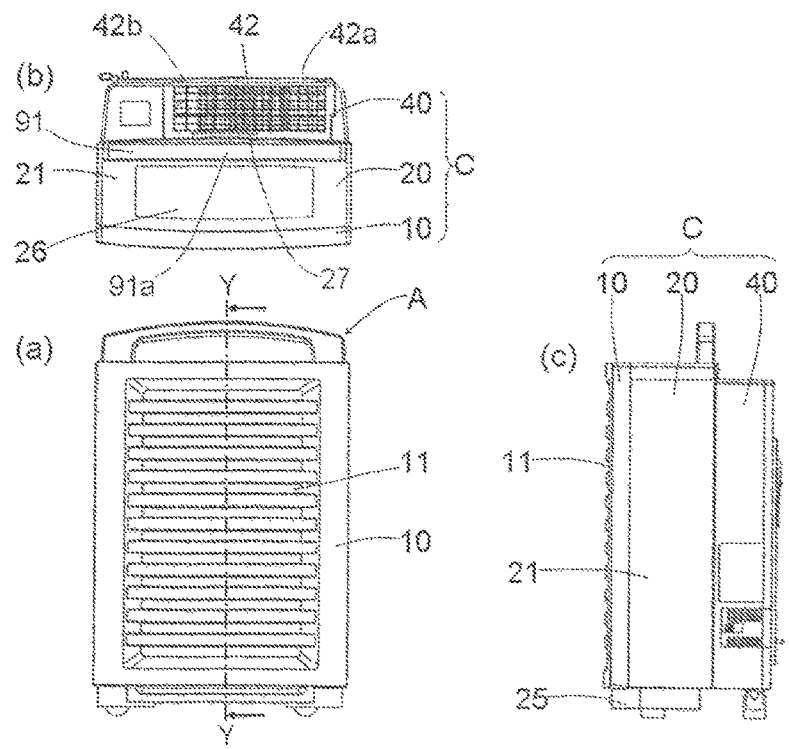
FIG. 1 shows three sides of a deodorizer A according to an embodiment of the present invention.
Figure 2:
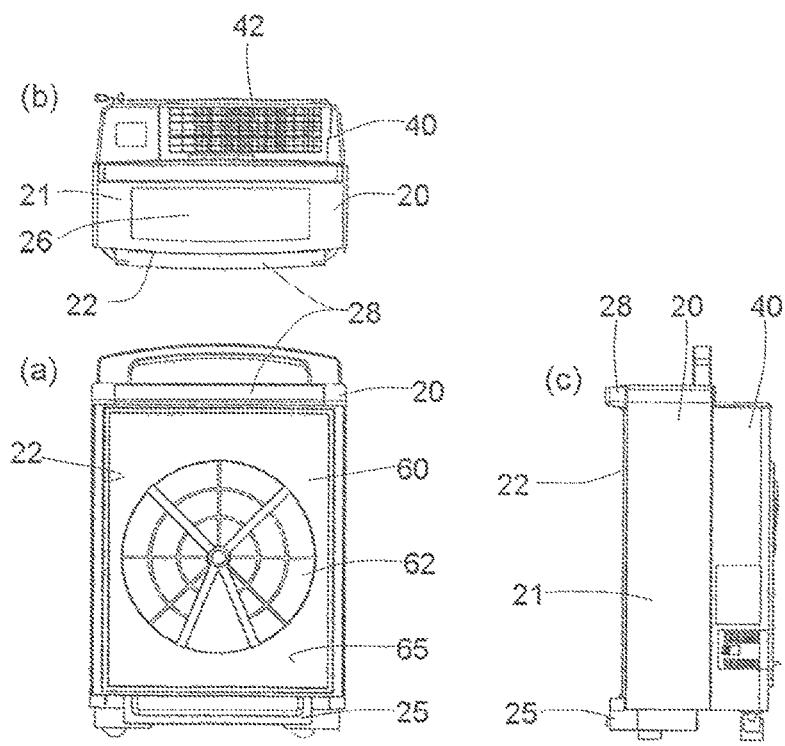
FIG. 2 shows three sides of the deodorizer A according to the embodiment of the present invention, with a front panel, a prefilter, and a HEPA filter described later being removed.
Figure 3:
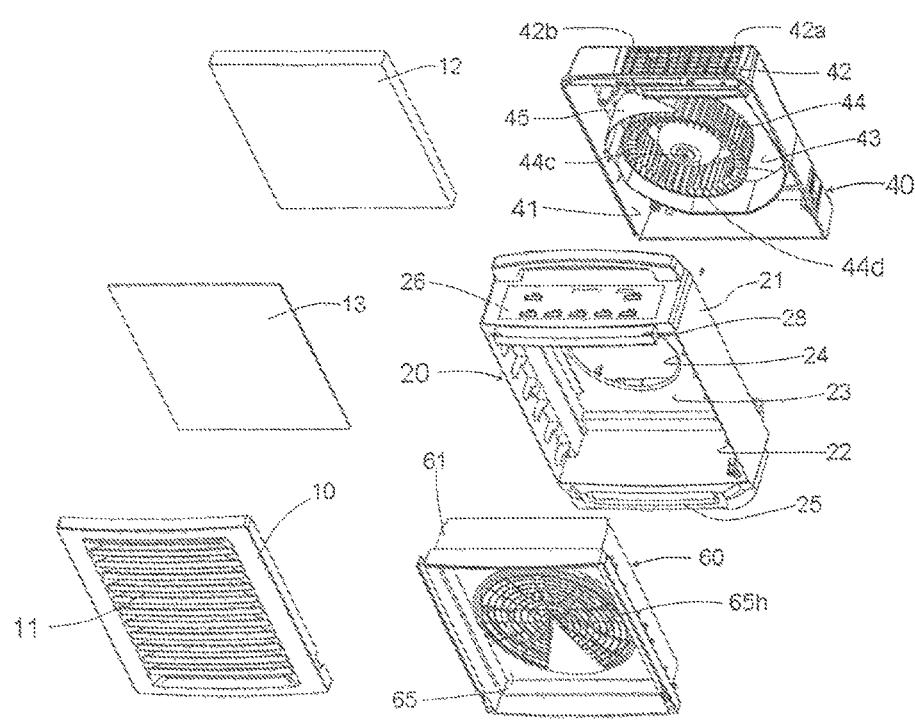
FIG. 3 is an exploded perspective view of the deodorizer A.
Figure 4:
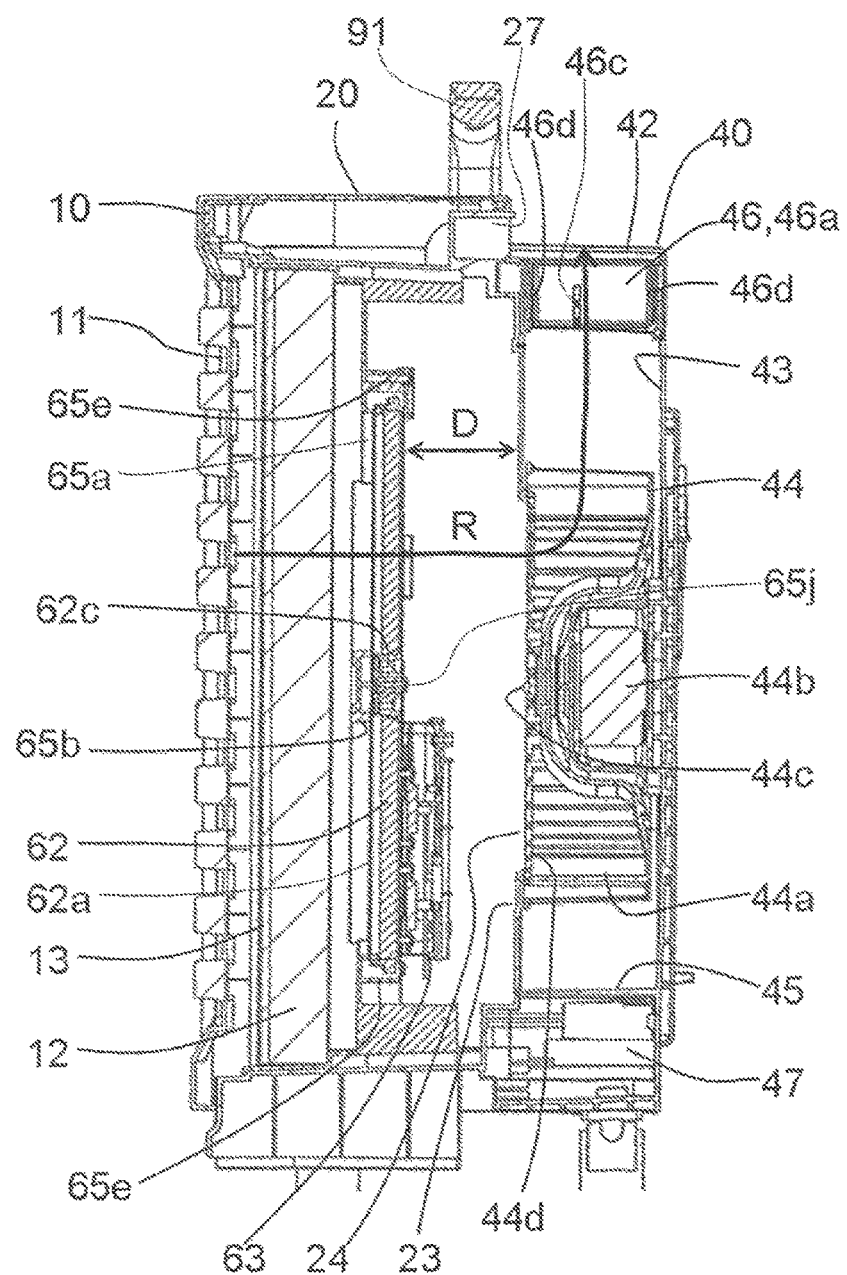
FIG. 4 is a vertical sectional view of the deodorizer A cut along Y-Y in FIG. 1.

FIG. 1 shows three sides of a deodorizer A according to an embodiment of the present invention, and FIG. 1(a) is a front view, FIG. 1(b) is a plan view, and FIG. 1(c) is a right side view. FIG. 2 shows three sides of the deodorizer A according to the embodiment of the present invention, with a front panel, a prefilter, and a HEPA filter described later being removed, and FIG. 2(a) is a front view, FIG. 2(b) is a plan view, and FIG. 2(c) is a right side view. FIG. 3 is an exploded perspective view of the deodorizer A. FIG. 4 is a vertical sectional view of the deodorizer A cut along Y-Y in FIG. 1. Now, with reference to FIGS. 1 to 4, a configuration of the deodorizer A will be described.

The deodorizer A as an air cleaner according to this embodiment includes a body case C that forms an outer shell, and various functional parts such as a deodorizing portion 60 provided in the body case C. The body case C has a shape of a box made of resin, and includes a plurality of parts such as a front panel 10, a front case 20, and a rear case 40. Now, configurations of these parts will be described in detail.

The front case 20 has a rectangular shape on front view, and includes a casing-like frame 21 with a depth as a base. A rectangular front opening 22 is formed in a front surface of the frame 21, and an opening in a rear surface is covered with a partition plate 23. A circular rear opening 24 that opens rearward is formed in the partition plate 23. Specifically, the front case 20 has the front opening 22 and the rear opening 24 communicating with each other. The rear opening 24 in the partition plate 23 forms a bell mouth around a fan opening 44d of a blowing fan 44 described later.

A lower protrusion 25 is formed on a lower side of the frame 21 of the front case 20 so as to generally protrude forward of left and right sides. An upper protrusion 28 is formed on an upper side of the frame 21 so as to protrude forward of the left and right sides. An operation portion 26 including a plurality of operation buttons or LEDs that form a display portion are provided on an upper front side of the upper side of the frame 21. Correspondingly to the operation portion 26, an operation board (not shown) on which the operation buttons or the LEDs are mounted is provided on an upper inner side of the upper side of the frame 21. The operation board is electrically connected to a controller 47 described later.

The front panel 10 has a rectangular shape on front view and is formed to cover the front opening 22 of the front case 20 from front. Laterally extending slits are formed in a front surface of the front panel 10, thereby forming an air inlet 11 that provides communication between front and rear of the front panel 10. Specifically, the front panel 10 ensures air permeability so that air can flow through the front panel 10 in a front-rear direction.

The rear case 40 has a rectangular shape on front view, and has a shape of a box including a front opening 41 that opens in a front surface, an opening to be an air outlet 42 formed in an upper surface, and a closed rear surface 43. The blowing fan 44 as blowing means for taking indoor air into an air cleaner, and a scroll-shaped partition plate 45 that forms an air trunk for guiding the air flowing down from the blowing fan 44 to the outlet 42 are provided on the rear surface 43. A controller 47 that controls each part of the deodorizer A based on a preset program is provided in a space formed below the partition plate 45 by the rear case 40 and the partition plate 45. Further, a louver 46 for changing a wind direction of air blowing out of the outlet 42 into a room or for closing the outlet 42 is provided near the outlet 42 in an upper part inside the rear case 40. A lattice is mounted to the opening of the outlet 42 so that the louver 46 is not directly touched.

The blowing fan 44 is configured as a multi-blade fan (sirocco fan) in which many blades 44a having a width in a rotational direction are mounted to positions at a preset radius from a rotating shaft. In the blowing fan 44, a motor 44b for rotationally driving the blades 44a is mounted to the rear surface 43 of the rear case 40 so that the rotating shaft 44c faces forward and extends horizontally.

A fan opening 44d surrounded by the blades 44a opens forward. As such, the blowing fan 44 is mounted to the rear case 40, thus the blowing fan 44 sucks air from the fan opening 44d facing forward in an axial direction of the rotating shaft 44c, and discharges the air radially of the blowing fan 44 including upward of the blowing fan 44.

The partition plate 45 stands on the rear surface 43 of the rear case 40 substantially perpendicularly thereto so as to surround the blowing fan 44, and has one end connected to a right end 42a of the outlet 42 and the other end connected to a left end 42b of the outlet 42. Specifically, the partition plate 45 is placed in the rear case 40 so as to surround the blowing fan 44 and have the ends opening outward from the outlet 42.

The louver 46 includes a plurality of plate-like wind direction plates 46a, a link mechanism 46c that connects the plurality of wind direction plates 46a and moves the wind direction plates 46a to a preset angle, and a driving portion (not shown) such as a motor for driving the link mechanism 46c. In the louver 46, the plurality of plate-like wind direction plates 46a are arranged in parallel with each other at intervals in the opening of the outlet 42, and each wind direction plate 46a is journaled on the outlet 42 by shafts 46d formed at opposite ends of the wind direction plate 46a. The driving portion for driving the link mechanism 46c is connected to the controller 47 described later. The controller 47 drives the driving portion according to a program for a state of the deodorizer A to change the direction of the louver 46.

Figure 5:
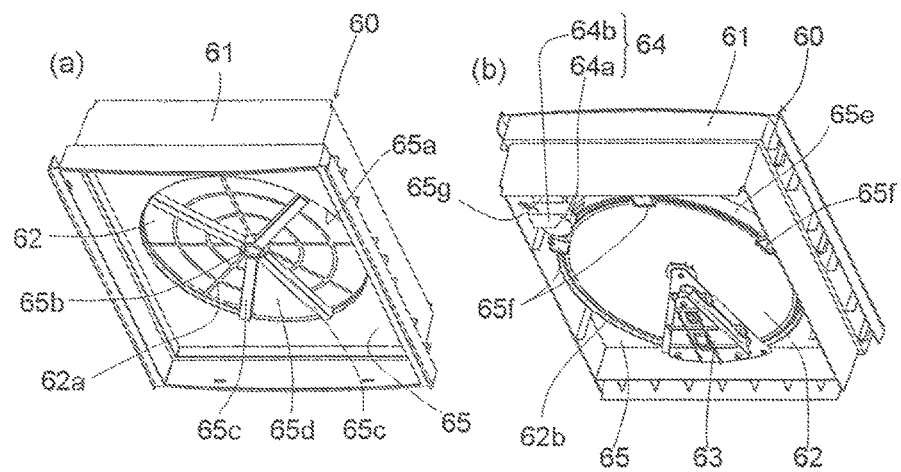
FIG. 5 is a perspective view of a deodorizing portion of an air conditioner according to an embodiment of the present invention.
Figure 6:
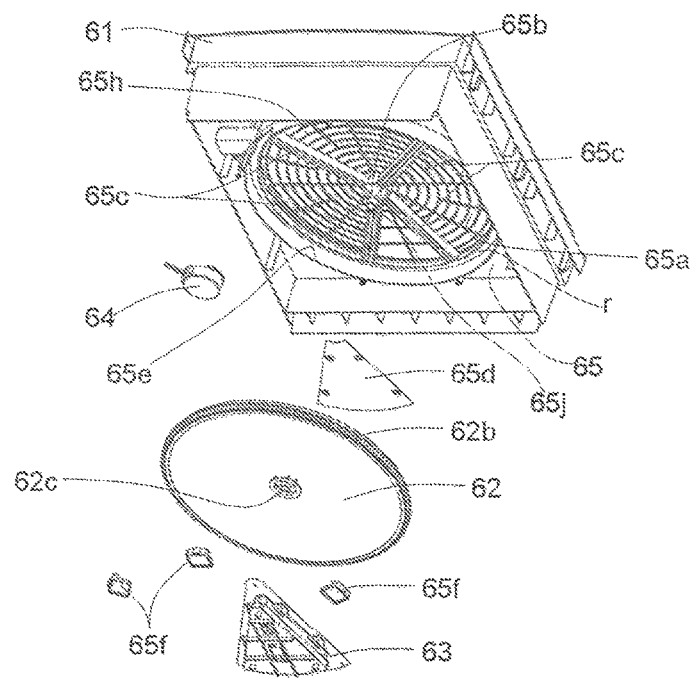
FIG. 6 is an exploded perspective view of the deodorizing portion of the air conditioner according to the embodiment of the present invention.

Next, with reference to FIGS. 5 and 6, a configuration relating to the deodorizing portion 60 will be described. FIG. 5 is a perspective view of a deodorizing portion of an air conditioner according to an embodiment of the present invention, FIG. 5(a) is a perspective view of the deodorizing portion seen from front, and FIG. 5(b) is a perspective view of the deodorizing portion seen from rear. FIG. 6 is an exploded perspective view of the deodorizing portion of the air conditioner according to the embodiment of the present invention. As shown in FIGS. 5 and 6, the deodorizing portion 60 causes indoor air having taken into the deodorizer A to pass therethrough and removes an odor from the air. The deodorizing portion 60 includes a casing body 61 as a base on which various parts are provided, deodorizing means 62, heating means 63 for locally heating the deodorizing means 62, and driving means 64 as position changing means for moving the deodorizing means 62 to change a relative positional relationship of the heating means 63 and a facing part of the deodorizing means. Now, these configurations will be sequentially described.

First, the casing body 61 is configured as a casing-like frame having a rectangular shape on front view and having a depth. An outer shape of the casing body 61 is sized so that the casing body 61 can be fitted in the front opening 22 of the front case 20. In the casing body 61, an inner partition plate 65 is provided so as to obstruct an opening of the casing body 61 (so as to partition the opening into front and rear). A circular opening 65a that provides communication between front and rear of the casing body 61 is formed in the inner partition plate 65. A central support 65b is located at a center of the opening 65a, and a plurality of beams 65c are formed radially extending from the central support 65b and connecting to an opening edge of the opening 65a. A shaft 65j protruding rearward is provided on the central support 65b. A casing 65h that allows air to flow into the opening 65a is provided in front of the opening 65a. The casing 65h prevents a user from directly touching the deodorizing means 62 described later. In FIG. 5, the casing 65h is not shown for clarifying each part.

Further, a ring-like guide portion 65e standing rearward so as to surround the opening 65a is formed on a back (rear) surface of the inner partition plate 65. Receivers 65f that receive the deodorizing means 62 described later are provided on an edge of the guide portion 65e so as to protrude inward of the opening 65a. The guide portion 65e is offset outwardly by a gap r from the opening edge of the circular opening 65a. The ring formed by the guide portion 65e has a diameter such that the ring can hold therein the deodorizing means 62 described later.

A fan-like region below the central support 65b of the opening 65a in the inner partition plate 65, which is formed by opening angles laterally equally spreading with respect to the central support 65b at the center, is covered with a fan-like lid 65d. The lid 65d is made of stainless, and secured by a screw or the like to the beam 65c from a rear (back) side of the inner partition plate 65. The lid 65d is placed to face the heating means 63 described later, and sized to cover a heater 63a of the heating means 63 when facing the heater 63a. Specifically, the heating means 63 and the lid 65d face each other to form a heating space for the deodorizing means 62 described later. A heat-resistant black paint is applied to the lid 65d in order to increase thermal emissivity.

Next, the configuration of the deodorizing means 62 as an essential portion of the present invention will be described. The deodorizing means 62 is a deodorizing filter having a disc-like planar shape, and configured by applying a catalyst to a honeycomb core of ceramic or aluminum having a plurality of openings like honeycomb openings or by impregnating the honeycomb core or other carrier with the catalyst, using a binder. The catalyst used has a nature of oxidatively decomposing an odorous component (particularly, ammonia component) by heating, such as a platinum-based catalyst or a catalyst containing manganese.

Specifically, the deodorizing means 62 is configured by adding an adsorbent that does not oxidatively decompose an adsorbed material and a catalyst component that oxidatively decomposes the adsorbed material to a carrier. The adsorbent is preferably composed of hydrophobic zeolite having a silica-alumina ratio of at least 60, zinc oxide, or both of them. Also, the catalyst component is preferably composed of manganese oxide.

Here, zeolite is a generic term for crystalline porous aluminosilicate, and refers to natural zeolite, and also synthetic zeolite such as mordenite, ferrierite, ZSM-5, A, X, L, Y, or beta type zeolite.

Zinc oxide refers to a compound with oxygen atoms or molecules added to zinc atoms in zinc oxide or the like. Zinc oxide is generally suitable for removing sulfide.

Manganese oxide refers to a compound with oxygen atoms or molecules added to manganese atoms in manganese oxide or manganese dioxide or the like. Manganese oxide acts as a catalyst, and is also suitable for removing some odor materials, for example, sulfide.

An opening portion 62c is formed in a center of the deodorizing means 62, and a frame 62a made of stainless for holding the deodorizing means 62 is provided on a front surface. Here, as described above, the deodorizing means 62 has a honeycomb core shape, and a preset opening is formed in the frame 62a provided on the front surface, thereby allowing air to flow through the deodorizing means 62 in a front-rear direction.

Further, a gear portion 62b is provided at a peripheral edge of the deodorizing means 62 so as to surround the deodorizing means 62. A diameter of the deodorizing means 62 including the gear portion 62b is larger than a diameter of the circular opening 65a formed in the inner partition plate 65.

Figure 7:
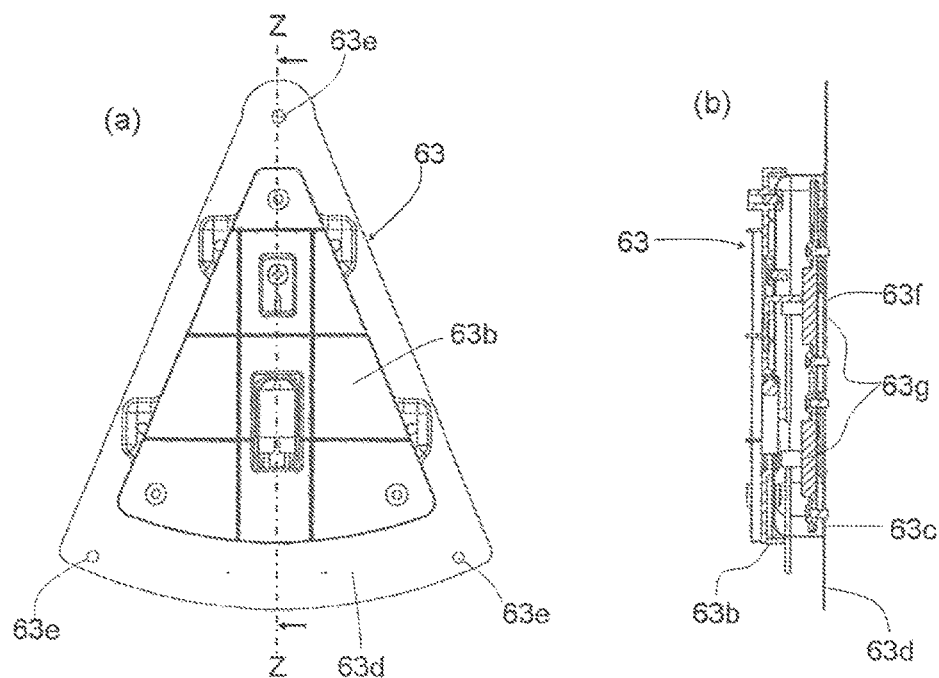
FIG. 7 shows the heating means for the deodorizer according to the embodiment of the present invention.
Figure 8:
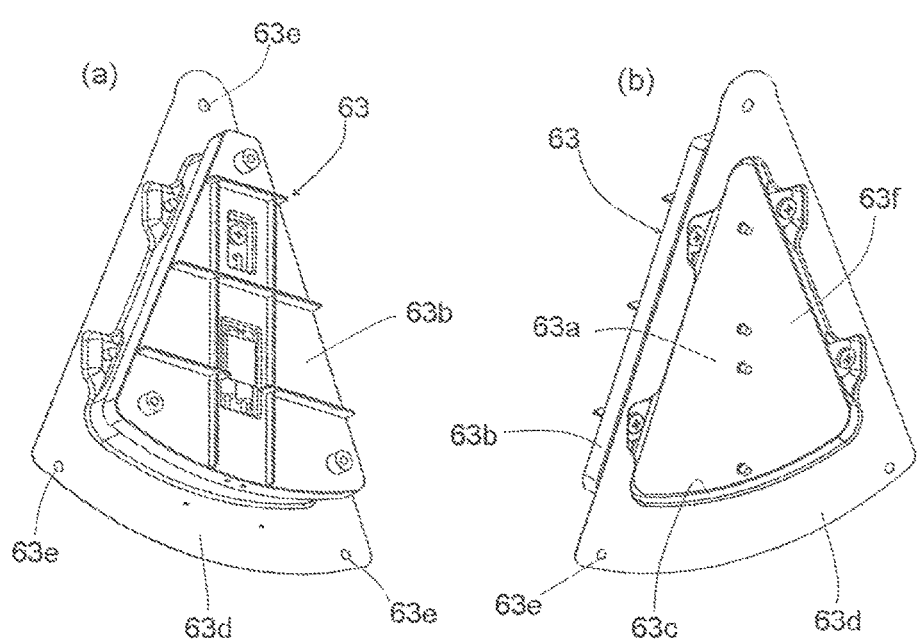
FIG. 8 is a perspective view of the heating means for the deodorizer according to the embodiment of the present invention.

Next, with reference to FIGS. 7 and 8, a configuration of the heating means 63 will be described. FIG. 7 shows the heating means for the deodorizer according to the embodiment of the present invention, FIG. 7(a) is a back view, and FIG. 7(b) is a vertical sectional view of the heating means cut along Z-Z in FIG. 7(a). FIG. 8 is a perspective view of the heating means for the deodorizer according to the embodiment of the present invention, FIG. 8(a) is a perspective view of the heating means seen from back, and FIG. 8(b) is a perspective view of the heating means seen from front.

As shown in the drawings, the heating means 63 includes a heater 63a as heating means for heating the deodorizing means 62, and a case 63b that forms an internal space for housing the heater 63a therein. The heater 63a is electrically connected to the controller 47, and controlled to be energized in accordance with an operation state of the deodorizer A. The heater 63a includes a plate-like heat generating portion 63f, and a heater portion 63g for heating the heat generating portion 63f. The heat generating portion 63f has a fan-like planar shape, and a heat-resistant (black) paint for increasing thermal emissivity of heat received from the heater portion 63g is applied to a surface thereof. With such a configuration of the heater 63a, the plate-like heat generating portion 63f receives heat generated from the heater portion 63g and radiates the heat from the entire plate surface, thereby evenly heating the deodorizing means 62 facing the heater 63a. A heating capability and an energizing time or the like of the heater 63a are set so that a portion of the deodorizing means 62 facing the heater 63a with a gap therebetween can be heated to a temperature at which an odor adsorbed by the deodorizing means 62 can be removed. As the heater 63a, a PTC heater that is semiconductor ceramic mainly containing barium titanate is used. The PTC heater is a heater that has self-temperature-controllability and does not require temperature control from outside. Thus, using the PTC heater eliminates the need for intermittent control as needed by a thermostat, thereby allowing stable use without generating sparks or noise.

The case 63b has a recess 63c for holding the heater 63a therein, and a flange portion 63d extending from a peripheral edge of an opening of the recess 63c. The recess 63c has a fan shape matching the planar shape of the heater 63a, and the heater 63a is provided in the recess 63c so as to face the opening of the recess 63c. The flange portion 63d has a screw hole 63e through which a screw is passed when the heating means 63 is mounted to a preset position. The heating means 63 configured as described above has a fan-like planar shape so as to conform to the shape of the heat generating portion of the heater 63a, and the opening of the recess 63c also has a fan shape.

Next, with reference to FIGS. 5 and 6, a configuration of the driving means 64 will be described. The driving means 64 is position changing means for moving the deodorizing means 62 to change a relative positional relationship between the heating means 63 and the facing part of the deodorizing means 62, that is, change a part of the deodorizing means 62 facing the heating means 63. The driving means 64 includes a motor 64a, and a bracket 64b that holds the motor 64a. A gear is mounted to a rotating shaft of the motor 64a. The motor 64a is electrically connected to the controller 47, and controlled to be energized in accordance with an operation state of the deodorizer A.

The deodorizing means 62, the heating means 63, and the driving means 64 described above are mounted to the casing body 61 to configure the deodorizing portion 60. Now, with reference to FIGS. 4 to 6, the configuration of the deodorizing portion 60 to which the deodorizing means 62, the heating means 63, and the driving means 64 are mounted will be described.

The deodorizing means 62 is rotatably fitted on the shaft 65j provided on the central support 65b of the casing body 61 with the opening portion 62c being a bearing. Thus, the deodorizing means 62 is placed in the guide portion 65e formed on the back (rear) surface of the casing body 61 rotatably with respect to the casing body 61 with the deodorizing means 62 facing the opening 65a. The receivers 65f that receive the deodorizing means 62 are mounted to an edge of the guide portion 65e so as to protrude inward of the opening 65a. The receivers 65f hold the rear (back surface) of the deodorizing means 62 to the extent that movement of the deodorizing means 62 in a rotational direction is not significantly inhibited.

The configuration for holding the deodorizing means 62 is not limited to the configuration in which the deodorizing means 62 is rotatably secured to the shaft 65j provided on the central support 65b, but may be, for example, a configuration in which the deodorizing means 62 is held using the guide portion 65e.

The heating means 63 is mounted to cover a part of the deodorizing means 62 with the deodorizing means 62 being placed in the casing body 61. Specifically, the heating means 63 is placed to span a lower part from the center of the deodorizing means 62 so as not to prevent rotation of the deodorizing means 62. In this state, the opening of the recess 63c in which the heater 63a is provided faces forward so that the heater 63a of the heating means 63 directly closely faces the deodorizing means 62. The heating means 63 is secured by a screw to mounting positions formed on the central support 65b located in the opening portion 62c of the deodorizing means 62, and the inner partition plate 65 located outside the deodorizing means 62. In this state, the heating means 63 and the lid 65d face each other with the deodorizing means 62 therebetween.

With the configuration as described above, the heating means 63 is secured to the casing body 61 without inhibiting movement of the deodorizing means 62 in the rotational direction (that is, without contact with the deodorizing means 62). The heating means 63 and the lid 65d face each other and are placed in the casing body 61, and thus a space for storing heat from the heater 63a is formed with the deodorizing means 62 being provided between the heating means 63 and the lid 65d.Further, since a paint to increase thermal emissivity is applied to the heat generating portion 63f, heat received from the heater portion 63g is efficiently radiated. As such, the heating means 63 is configured to efficiently locally heat the facing part of the deodorizing means 62.

The driving means 64 is placed on a back surface of the inner partition plate 65 of the casing body 61, in a part between the opening 65a and a corner 65g of the inner partition plate 65. More specifically, a bracket 64b holding the motor 64a is secured to the inner partition plate 65. In this case, the motor 64a is placed so that the gear mounted to the rotating shaft of the motor 64a meshes with the gear portion 62b provided on the deodorizing means 62. The driving means 64 is preferably placed in a part between a corner 65g on an upper side away from the heating means 63 among four corners 65g and the opening 65a.

As such, with the placement of the driving means 64, energization control by the controller 47 drives the motor 64a to allow the deodorizing means 62 to be rotated with respect to the casing body 61. Thus, the part of the deodorizing means 62 facing the heating means 63 can be changed, that is, the relative positional relationship between heating means 63 and the deodorizing means 62 can be changed. Since the driving means 64 is provided between the opening 65a and the corner 65g, a dead space around the opening 65a formed in the rectangular inner partition plate 65 can be effectively used. Further, the driving means 64 is provided away from the heating means 63, and thus the driving means 64 is less influenced by the heat generated from the heating means 63.

The front panel 10, the front case 20, the rear case 40, and the deodorizing portion 60 configured as described above are assembled with other functional parts as described below to configure the deodorizer A.

As shown in FIG. 3, the rear case 40 is mounted to the rear surface of the front case 20 with the front opening 41 facing forward. At this time, the fan opening 44d of the blowing fan 44 provided in the rear case 40 faces the rear opening 24 formed in the partition plate 23 provided in the front case 20. The center of the rear opening 24 conforms to an axis of the rotating shaft of the blowing fan 44 in a front-rear direction.

The deodorizing portion 60 is mounted to the front case 20 by the casing body 61 being inserted from the front opening 22 in the front case 20 into the front case 20 and an outer periphery of the casing body 61 being held in the front case 20. As such, with the deodorizing portion 60 being mounted to the front case 20, the rear side of the deodorizing portion 60 (the side to which the heating means 63 is mounted) faces the rear opening 24 of the front case 20. Thus, the heating means 63 is located between the deodorizing means 62 and the rear opening 24.

Here, as shown in FIG. 4, the partition plate 23 and the rear opening 24 of the front case 20 that form a bell mouth around the fan opening 44d of the blowing fan 44 face the deodorizing means 62 with a preset gap D therebetween so as not to prevent air from flowing from the deodorizing means 62 to the rear opening 24. The heating means 63 is located in the gap D thus formed.

As shown in FIG. 3, a HEPA filter 12 having a size similar to that of the opening in the casing body 61 is provided in the casing body 61 of the deodorizing portion 60 mounted to the front case 20. The HEPA filter 12 is a filter for removing fine dust such as pollen, mite feces, mold spores, or house dust contained in air. Also, a prefilter 13 is provided on a front side of the HEPA filter 12 so as to cover the HEPA filter 12. The prefilter 13 is a coarse filter for previously removing large dust contained in air before filtration of the air using the HEPA filter, and for keeping a long-term effect of the HEPA filter. On a front side of the prefilter 13, the front panel 10 is provided between the upper protrusion 28 and the lower protrusion 25 of the front case 20. As such, the front panel 10, the prefilter 13, the HEPA filter 12, the deodorizing portion 60, the front case 20, and the rear case 40 are assembled to configure the deodorizer A.

Next, an air cleaning operation of the deodorizer A configured as described above will be described. As shown in FIG. 4, an air duct R that takes in, cleans, and deodorizes indoor air and then releases the air into the room is formed in the deodorizer A. The air duct R will be described in line with an air cleaning operation state of the deodorizer A and a flow of air taken into the air duct.

First, when a user operates the operation portion 26 to input to the controller 47, a program for operating the deodorizer A is executed. When the operation is started, the blowing fan 44 is driven, a suction force to take indoor air from the inlet 11 into the deodorizer A is generated, and the indoor air flows into the inlet 11. The air taken from the inlet 11 flows rearward in the deodorizer A, large dust is removed from the air by the prefilter 13, and then fine dust is removed by the HEPA filter 12.

Next, the air from which dust has been removed further flows rearward and reaches the deodorizing portion 60, passes through the opening 65a, and then reaches the deodorizing means 62 placed to face the opening 65a. The deodorizing means 62 has many honeycomb-shaped openings extending from a front surface to a back surface, and carries, on its front surface, an adsorbent and a catalyst component that adsorb an odor.

Thus, the air containing an odor passes through the honeycomb-shaped openings when passing from the front side to the back side of the deodorizing means 62, and the adsorbent and the catalyst component carried by the deodorizing means 62 adsorb the odor contained in the air, and thus remove the odor from the air. "Remove the odor from the air" includes a state where the odor is completely removed from the air, and also a state where the odor is reduced from a state before the air passes through the deodorizing means 62. Here, the deodorizer A is continuously operated as described above, thus adsorbed odors accumulate in the deodorizing means 62, and a deodorizing capability of the deodorizing means 62 is reduced with increasing adsorbed odors.

Next, the air from which the dust and the odor are removed further flows rearward from the deodorizing means 62, passes through the rear opening 24 that opens in the partition plate 23 of the front case 20, and flows to the blowing fan 44 placed to face the rear opening 24. The air flowing to the blowing fan 44 flows down into the fan opening 44d surrounded by the blades 44a from axial front of the blowing fan 44, and is discharged to the outside of the blowing fan 44 radially of the blowing fan 44 including upward of the blowing fan 44.

The air discharged from the blowing fan 44 is guided to the outlet 42 by the partition plate 45 of the rear case 40, a wind direction is adjusted when the air passes through the louver 46, and then the air is blown out from the outlet 42 upward of the deodorizer A as clean air from inside the deodorizer A.

As such, the air duct R connects to a rear of the body of the deodorizer A horizontally from the inlet 11, turns upward at the rear, and reaches the outlet 42. Specifically, in the air duct R, with reference to the air flow, the prefilter 13 and the HEPA filter 12 as dust filtration filters are placed upstream of the deodorizing means 62, and a bent portion at which the air flow is bent upward is formed downstream of the deodorizing means 62. A sirocco fan as the blowing fan 44 is located in the bent portion. The sirocco fan takes in air in a direction of the rotating shaft of the fan, and discharges the taken air radially of the fan. This allows a linear flow of the indoor air to be formed from the front surface to the rear of the body case C, and allows the wind direction to be efficiently changed toward the outlet 42.

The front surfaces of the deodorizing means 62, the prefilter 13, the HEPA filter 12, and the fan opening 44d of the blowing fan 44 are placed perpendicularly to the direction of air flowing in the air duct R. Thus, the air flows straight until it passes through the deodorizing means 62, and the air hits each filter surface perpendicularly thereto, thereby allowing a satisfactory air flow.

The opening 65a is located at a middle in a vertical direction of the front of the body case C so that a relationship between a projection area X on front view of the body case C and an area Y of the opening 65a on front view is $Y \geq 0.6X$.

If the air cleaning operation (deodorizing operation) is performed for long hours, the deodorizing means 62 adsorbs a large volume of odors and is gradually reduced in deodorizing performance. In the deodorizer A of this embodiment, when the deodorizing performance of the deodorizing means 62 is reduced, a regenerating operation for restoring the performance is performed. Now, the regenerating operation will be described in more detail.

The controller 47 performs a regenerating operation of the deodorizing means 62 at preset timing. The preset timing may be, for example, timing when a cumulative operation time from a start of operation or completion of a former regenerating operation exceeds a preset time (preferably, once or more in 24 hours).

When the regenerating operation is started, the controller 47 energizes the heater 63a of the heating means 63. Thus, the heater 63a generates heat, and a temperature of the part of the deodorizing means 62 facing the heater 63a is maintained at a preset heating temperature for a preset heating time. The temperature and time of the deodorizing means 62 in the regenerating operation are preferably set to a temperature and time sufficient for removing the odor adsorbed by the deodorizing means 62. At this time, since the heating means 63 and the deodorizing means 62 face each other with air therebetween, there is a difference between the temperature input to the heating means 63 and the temperature of the deodorizing means 62. This is because of cooling by an air space, and thus the temperature needs to be set in view of that.

When the temperature of the heating portion of the deodorizing means 62 is increased to a heating temperature α, a configuration is preferably provided that detects a temperature using temperature detection means (not shown) such as a thermistor placed in the heating means 63, and checks that the temperature does not suddenly increase. The sudden temperature increase herein refers to that, for example, when using a heater 63*a* that increases the temperature 3° C. to 5° C. per 10 seconds, a detected temperature by the temperature detection means increases at the same or higher speed than the above. Since the deodorizing means 62 is heated by the heater 63*a*, the temperature may be normally increased by afterheat when the energization to the heater 63*a* is stopped, but the temperature is unlikely to be increased at the speed equal to or higher than that during the energization to the heater 63*a*. Thus, when such a temperature increase is detected, the heating means 63 is immediately stopped to finish the regenerating operation, and the temperature increase is notified to the user by sending an error message or the like. If the sudden temperature increase is not detected, energization to the heater 63*a* is restarted. As such, the heating temperature is maintained at a predetermined temperature, thereby preventing degradation of the deodorizing means due to an excessive temperature increase caused by an excessive oxidation reaction. Also, an unintended intermediate product, for example, a material that is easily perceived as a worse odor than an original odor material such as acetic acid as an oxidative decomposition product of ethanol and also has high odor intensity is prevented from being excessively produced on the deodorizing means and excessively re-released when the deodorizer performs a normal deodorizing operation.

When the regenerating operation of the part facing the heating means 63 is finished, the controller 47 operates the driving means 64 for rotating the deodorizing means 62 to rotate the deodorizing means 62 by a preset angle. This operation causes the part of the deodorizing means 62 facing the heating means 63 and having been subjected to heating to be displaced with respect to the heating means 63 in the rotational direction. Thus, the part of the deodorizing means 62 having been subjected to heating is dislodged from the position between the heating means 63 and the lid 65*d*, and a part of the deodorizing means 62 having newly adsorbed a large volume of odors is located between the heating means 63 and the lid 65*d*. Such an operation is performed until the deodorizing means 62 makes one turn, thereby sequentially heating the entire deodorizing means 62. Thus, the entire deodorizing means 62 can be divided and regenerated rather than be heated and regenerated at one time, thereby preventing acetic acid or other gas components as an intermediate product of an oxidative reaction of ethanol produced at one time from being re-released by the regenerating operation.

The rotation angle of the deodorizing means 62 is preferably equal to or smaller than the opening angle of the fan-like heater 63*a*. Setting such a rotation angle allows every part of the deodorizing means 62 to necessarily stay in front of the heater 63*a* and be heated during one turn of the deodorizing means 62. Also, the deodorizing means 62 may be moved immediately after heating, or immediately before a next air cleaning operation.

In the regenerating operation described above, the blowing fan 44 as the blowing means may be operated or stopped. Specifically, if the blowing fan 44 is not operated during the regenerating operation, the heating temperature is easily maintained and thus the oxidative decomposition reaction can be stably facilitated. On the other hand, if the blowing fan 44 is operated during the regenerating operation, more input is required to heat the surface of the deodorizing means 62 to a preset heating temperature, while an odor desorbed from the surface of the deodorizing means 62 is easily removed. In particular, operating the blowing fan 44 preferably facilitates desorption of an alcohol material such as ethanol adsorbed by the adsorbent from the surface of the deodorizing means 62. Ethanol is a material that is less likely to become a problem as a foreign odor, and if adsorbed ethanol is desorbed and removed, chances of ethanol reacting with the catalyst component of the deodorizing means 62 to produce acetic acid can be reduced.

The heating temperature α in the regenerating operation is preferably higher in terms of facilitating oxidative decomposition of an odor material. Specifically, in the regenerating operation for increasing the temperature of the deodorizing means 62 to the heating temperature α required for regeneration as in this embodiment, oxidative decomposition of the adsorbed material can be more facilitated with increasing heating temperature α. However, when the heating temperature α is high, a reaction with abnormal heating may be facilitated on the deodorizing means 62 to degrade the deodorizing means 62 or the like due to an excessive temperature increase.

Thus, in the regenerating operation in this embodiment, the heating temperature α is set to 200° C. or less, and more preferably 150° C. or less as a temperature at which the deodorizing means 62 is not degraded due to an excessive temperature increase. However, if the surface of the deodorizing means 62 is heated at a relatively low temperature of 200° C. or less, the odorous component adsorbed by the deodorizing means is not completely oxidatively decomposed to carbon dioxide due to a reduction in oxidative decomposition ability of the catalyst component, and the reaction may stop at a stage of an intermediate product with a lower odor threshold. For example, ethanol often detected in indoor environments such as hospitals is decomposed via acetaldehyde and acetic acid into carbon dioxide and water, and a low heating temperature prevents development of a reaction of acetic acid and thereafter. The produced acetic acid is once adsorbed by the adsorbent, but is likely to be easily re-released at high humidity in ambient environment. Thus, although there is no problem in fine weather, acetic acid is re-released in rainy weather to provide blown-out air having a sour odor, which is likely to make the user of the deodorizer uncomfortable.

The heating time in the regenerating operation is preferably short, but too short a heating time prevents development of decomposition of an adsorbed material that reacts at a low oxidative decomposition reaction speed. Thus, the heating time is required sufficient for development of decomposition of the odor material to be adsorbed. A reaction of acetaldehyde as a decomposition product of ethanol being oxidatively decomposed to produce acetic acid develops in a relatively short time, but it is known that the reaction of acetic acid and thereafter is less likely to develop at a low temperature of 200° C. or less. Also, decomposition of ammonia having an odor of excrement requires a longer time than that required for production of acetic acid by decomposition. Thus, reducing the heating time does not always prevent production of an intermediate product such as acetic acid.

Thus, in the regenerating operation of the deodorizer A in this embodiment, by a combination of a proportion of manganese oxide carried by the deodorizing means 62, a heating temperature, and a heating time, a rate of conversion into acetic acid of the entire deodorizing means 62 is set to 15% or less on average. The average herein refers to an average per one cycle of the regenerating operation. In particular, in a heating and regenerating process, the heating temperature varies, and a constant rate of conversion into acetic acid cannot be always obtained. Also, the deodorizing filter significantly has unevenness in carrying, and when the deodorizing filter is cut into small pieces, all the pieces do not necessarily have the same rate of conversion into acetic acid. A sour odor is actually perceived after the odor is released in the room and starts to fill the room, and an instantaneous variation of the odor due to the variation in heating temperature or the unevenness in carrying is not perceived. For the above reasons, for the deodorizer A of this embodiment, the rate of conversion into acetic acid of the deodorizing means 62 is defined as an average. This can prevent ethanol adsorbed by the deodorizing means 62 from being oxidatively decomposed and re-released as acetic acid from the deodorizing means 62. Also, selecting an optimum catalyst can maintain the oxidative decomposition ability of a target odor.

Here, the rate of conversion into acetic acid represents a percentage of ethanol adsorbed by the catalyst being oxidatively decomposed into acetic acid at a preset temperature for a preset reaction time and released, and is expressed by the following expression:

Amount (molar amount) of released acetic acid/ amount (molar amount) of adsorbed ethanol× 100=rate of conversion into acetic acid [%]

The rate of conversion into acetic acid increases with increasing carried amount of manganese oxide as a catalyst. For the deodorizing means 62 in this embodiment, the carried amount and the heating time of manganese oxide are determined so that the heating temperature is less than 200° C., preferably 150° C. or less, and the rate of conversion into acetic acid of the entire deodorizing means 62 is within 15% on average. The rate of conversion into acetic acid can be measured by the following procedure.

First, a preset amount (molar amount) of ethanol is adsorbed by a structural component of the deodorizing means 62, and heated in an oxygen atmosphere by a batch testing system to a temperature reached by the deodorizing means 62 using the heating means. Then, an air component in the testing system after heating for a preset heating time is analyzed by a gas chromatography (GC) or the like to obtain an amount (molar amount) of acetic acid released into the oxygen atmosphere. Then, a ratio of the molar amount of released acetic acid to an initial molar amount of adsorbed ethanol is calculated as an average rate of conversion into acetic acid of the entire deodorizing means 62 during the heating time.

Given an actual use, a value of ethanol adsorbed by the deodorizing means 62 varies, and thus it is important that the rate of conversion into acetic acid does not exceed 15% under any conditions. Thus, the amount of ethanol adsorbed in the measurement descried above may sufficiently exceed the amount of adsorbed ethanol possible under a use environment of the deodorizer. Such an amount of adsorbed ethanol is, for example, preferably 0.05 µmol/mg or more for an amount of unit material. Also, the amount of oxygen in the measurement described above is desirably set supposing an equal amount of general atmosphere. For the deodorizer according to this embodiment 1, the amount of oxygen is set to 28 µmol. The heating temperature and the heating time in the measurement described above may be determined according to setting of the deodorizer. For example, for the deodorizer according to this embodiment 1, the heating temperature is 140° C. to 120° C. and the heating time is one hour as described later, and thus the heating temperature of 140° C. and the heating time of one hour are suitably set as measurement conditions for calculating the rate of conversion into acetic acid.

In the deodorizer A including the deodorizing means 62, the rate of conversion into acetic acid when the regenerating operation is actually performed can be measured by the following procedure. First, a preset amount (molar amount) of ethanol is adsorbed by a structural component of the deodorizing means 62, and a regenerating operation of the deodorizer is performed in an oxygen atmosphere by a batch testing system. In the regenerating operation, the deodorizing means 62 is heated based on the heating temperature and the heating time preset to the deodorizer A. Then, the air component in the testing system after completion of the regenerating operation is analyzed by a gas chromatography (GC) or the like to obtain an amount (molar amount) of acetic acid released into the oxygen atmosphere. Then, the ratio of the molar amount of released acetic acid to the initial molar amount of adsorbed ethanol is calculated as an average rate of conversion into acetic acid of the entire deodorizing means 62 during the heating time. The amount of adsorbed ethanol in this measurement is preferably 0.05 µmol/mg or more for an amount of unit material as described above. The amount of oxygen is preferably set to 28 µmol.

The deodorizer of the present invention has an object to prevent acetic acid adsorbed by the deodorizing means 62 from being desorbed and released from the outlet during a normal deodorizing operation, that is, while air formed by the blowing means passes through the deodorizing means 62. As one approach therefor, the rate of conversion into acetic acid of the deodorizing means 62 is noted.

A full amount of acetic acid adsorbed by the deodorizing means 62 is not released. Releasing is influenced by an amount of air passing through the deodorizing means 62 or humidity, and generally, an amount of desorbed acetic acid increases with increasing amount of air or increasing humidity. An acetic acid concentration in blown-out air from the deodorizer is expressed by the following expression:

Acetic acid concentration in blown-out air [mg/m^3]=(amount of conversion from ethanol into acetic acid on deodorizing means [mg/day]+amount of naturally-produced acetic acid in room [mg/day])×rate of re-releasing by blowing air/amount of blown-out air from deodorizer [m^3/min].

The acetic acid concentration in the blown-out air can be discussed as odor intensity by conversion into ppm using a conversion formula. Also, the "amount of conversion from ethanol into acetic acid on deodorizing means" is a value obtained by multiplying the amount of ethanol [mg/day] existing in the room and adsorbed by the deodorizing means by the rate of conversion into acetic acid described above, and refers to a part of acetic acid adsorbed on the deodorizing means. The "amount of naturally-produced acetic acid in room [mg/day]" refers to acetic acid naturally produced such as biologically derived one, and refers to acetic acid adsorbed on the deodorizing means like the "amount of conversion into acetic acid". For specific values, see various reports about investigations on-site actual measurement or indoor environments. The "rate of re-releasing by blowing air" refers to an amount of acetic acid re-released with respect to the amount of adsorbed acetic acid, and a value actually measured in view of conditions such as an amount of air of the deodorizer or a temperature and humidity of an installation place of the deodorizer is preferably used. Also for the "amount of blown-out air from deodorizer", an operation condition for each deodorizer is preferably referred to.

From the above calculation formula, a trial calculation can be performed of whether the acetic acid concentration in the blown-out air from the deodorizer is derived from ethanol in the room or from naturally-produced acetic acid. Thus, the present inventor has revealed that acetic acid derived from ethanol, that is, acetic acid produced by conversion of ethanol by an oxidative decomposition reaction significantly influences the acetic acid concentration in the blown-out air in environments such as hospitals always containing much ethanol.

The acetic acid concentration in the blown-out air by the calculation formula described above corresponds to an acetic acid concentration in the blown-out air when ethanol and acetic acid for one day are adsorbed. An acetic acid concentration in the blown-out air on a second day is calculated from a sum of acetic acid remaining on the deodorizing means 62 except acetic acid removed by a regenerating operation from acetic acid adsorbed on the first day, and ethanol and acetic acid adsorbed by the operation of the deodorizer on the second day, and this calculation is repeated thereafter with time. If a heating and regenerating rate, that is, a ratio of the amount of odor material removed from the deodorizing means 62 by heating to the amount of adsorbed odor material is assumed to be less than 100%, the acetic acid concentration in the blown-out air increases with time. However, after a lapse of a certain time, the amount of odor material adsorbed by the deodorizing means 62 and the amount of heated and regenerated odor material are balanced, and thus the concentration of acetic acid released into the blown-out air is balanced.

Figure 9:
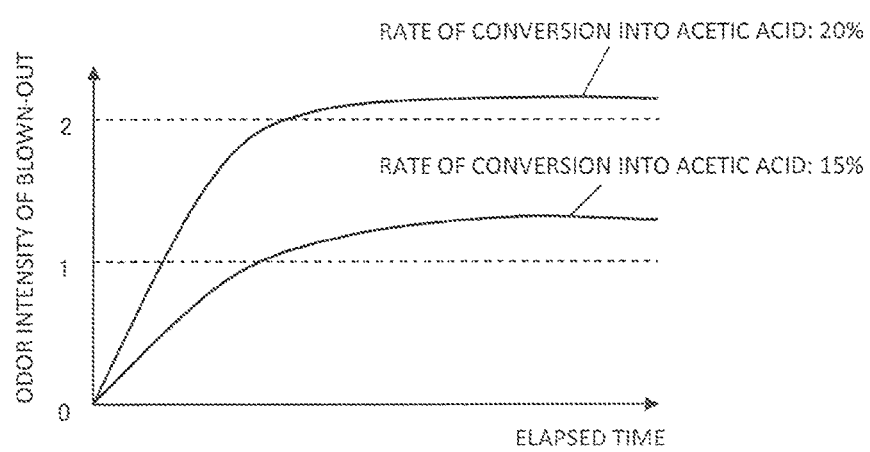
FIG. 9 shows changes with time of the concentration of acetic acid contained in the blown-out air.

FIG. 9 shows changes with time of the concentration of acetic acid contained in the blown-out air described above, and shows how the rate of conversion into acetic acid contributes to the acetic acid concentration. The amount of conversion from ethanol into acetic acid increases with increasing rate of conversion into acetic acid, and thus the amount of acetic acid adsorbed by the deodorizing means 62 for one day increases, thereby increasing the acetic acid concentration contained in the blown-out air. The example in FIG. 9 shows that the rate of conversion into acetic acid of the entire deodorizing means 62 is 15% or less on average, and thus for example, in the case where the deodorizer is continuously operated for ten hours in the room containing ethanol of less than 15 ppm, even if acetic acid produced by ethanol adsorbed by the deodorizing means 62 being oxidatively decomposed is re-released after the regenerating operation, particularly in a normal air cleaning operation in a high humidity environment, odor intensity of an blown-out odor is less than 2. On the other hand, the rate of conversion into acetic acid of 20% shows that the amount of acetic acid adsorbed by the deodorizing means 62 for one day is too large, and the acetic acid concentration in the blown-out air reaches the odor intensity of 2 or more with time, and the user of the deodorizer can perceive the odor of acetic acid in the blown-out air. The operation condition, for example, a flow amount of the deodorizer differs depending on deodorizers, and the odor intensity of 2 herein refers to the acetic acid concentration in the blown-out air from the deodorizer. Specifically, the blown-out air from the deodorizer is collected in a bag, and results are shown of evaluation by odor intensity converted from the concentration measured by a detection pipe, or by a six grades odor intensity measurement method.

The odor intensity is generally evaluated by the "six grades odor intensity measurement method", which is a testing method for determining odors by a sense of smell. The odor intensity grades are represented as 0: odorless, 1: odor barely perceivable (detection threshold), 2: weak perceivable odor (perception threshold), 3: odor easily perceivable, 4: strong odor, and 5: very strong odor.

Examples of proportions of catalysts or the like added to the deodorizing means 62 as the deodorizing filter are as described below. The following approaches are used to determine proportions of catalysts or the like for reducing a sour odor, that is, the rate of conversion into acetic acid.
(1) To increase oxidation performance, and facilitate decomposition into carbon dioxide.
(2) To suppress oxidation performance, and discharge alcohol as it is.
(3) To immediately release acetic acid before it is accumulated to be perceived by nose.

For (1), for example, an increase in heating temperature and an adjustment of heating time are conceivable. In Embodiment 1, the heating temperature is set to 140° C. to 120° C. and the heating time is set to one hour by comprehensive judgement of an influence on surrounding members, costs, energy saving performance, safety or the like. Specifically, the heating temperature and the heating time are determined by emphasizing factors other than an influence on performance for Embodiment 1. In particular, the heating time needs to be set within 16 hours in terms of usability, and is limited to 0.5 to 4 hours in view of degradation of the deodorizing means 62 due to heating.

For (2), in this embodiment 1, manganese oxide is selected as an oxidation catalyst. It is found that acetic acid is less produced with decreasing amount of catalyst, but reducing the amount of catalyst reduces removal performance of ammonia or sulfide. Then, in this embodiment 1, a weight percentage of manganese oxide is 5 wt % to 10 wt % with respect to carried components (catalyst components and adsorbent) in view of a balance with other odorous components.

For (3), in this embodiment 1, hydrophobic zeolite having a silica-alumina ratio of 60 or more is used as an adsorbent as described above. Since a hydrophilic material absorbs water, acetic acid is also adsorbed by a part absorbing water, which may cause variations in measurement data. Also, the hydrophilic material has a large adsorbing capacity, but accumulates acetic acid and releases the acetic acid at once if a limit is reached. On the other hand, a hydrophobic material does not have the disadvantage of the hydrophilic material as described above, and does not accumulate acetic acid. Thus, in this embodiment 1, even if the manganese oxide produces acetic acid, the acetic acid can be released before accumulated to such an extent that a sour odor is perceived. In particular, it is found that a guideline for the advantage descried above is a silica-alumina ratio of 60, which is limited in Embodiment 1.

In this embodiment 1, apart from manganese oxide, hydrophobic zeolite and a slight amount of zinc oxide account for 90 to 95 wt %. However, for example, other than hydrophobic zeolite, zinc oxide or the like, for example, may be mixed that is not active at 150° C. or less and has no oxidation performance.

In this embodiment 1, the proportions of manganese oxide and hydrophobic zeolite are as described above. However, situations differ depending on crystal structures of manganese oxide or hydrophobic zeolite, and thus the proportions are not limited to above in this embodiment 1. Specifically, the rate of conversion into acetic acid described above may be measured and an optimum proportion may be determined in view of a balance with target odorous component removing performance.

The parts of the deodorizer A are configured as described above to obtain advantages as described below.

With the deodorizer A of this embodiment, production of acetic acid as an oxidative decomposition product of ethanol can be prevented without reducing an adsorbing capacity of the deodorizing means 62. This can provide a deodorizer in which even in an environment containing much ethanol, a target odorous component can be adsorbed and removed in a short time, and the user can realize a deodorizing effect.

With the deodorizer A of this embodiment, the rate of conversion into acetic acid of the entire deodorizing means 62 is reduced to 15% or less on average. Thus, a regenerating operation does not cause acetic acid produced in a normal deodorizing operation to be re-released even at a low temperature at which a material (for example, acetic acid as an intermediate product of ethanol) having a lower odor threshold than an original odorous component and detected as a bad odor by a human is easily produced. Also, a deodorizer can be provided that allows the user to realize a deodorizing effect even in a regenerating operation at a relatively low temperature that is low temperature heating at less than 200° C. This can prevent a material adsorbed by the deodorizing means from causing an abnormal heat generating reaction as compared to high temperature heating and regenerating control, and thus prevent degradation or the like of the deodorizing means 62 due to an excessive temperature increase during the regenerating operation. Also, since there is no need to reduce the amount of added adsorbent, a deodorizer can be provided that allows adsorbing and removing performance to be realized even in a short time.

In the regenerating operation of the deodorizing means 62, it is preferable to previously heat the deodorizing means 62 at a lower temperature before the heating temperature a required for the regenerating operation is reached. This reduces an amount of remaining material that causes an excessive temperature increase when the heating temperature a that is a high temperature is reached, and thus prevents degradation of the deodorizing means 62 due to the excessive temperature increase. However, the temperature lower than the heating temperature α descried above must not cause the adsorbed odor material to be oxidatively decomposed to produce a large volume of bad odor materials having higher odor intensity, and detailed control specifications with a heating time need to be determined in view of a use environment or the like of the deodorizer.

Also, the regenerating operation of the deodorizing means 62 is preferably performed at appropriate intervals such as once or more in 24 hours. This allows the material adsorbed by the deodorizing means 62 to be easily released, and thus prevents an abnormal temperature increase. This is because, as the adsorbed material accumulates, an amount of heat generation caused by an oxidative decomposition reaction increases to easily cause an abnormal temperature increase even if the heater 63a is heated to the same temperature.

Also, with the deodorizer A of this embodiment, the relative positional relationship between the deodorizing means 62 and the heating means 63 that locally heats the deodorizing means 62 is changeable, thereby reducing a size of the heating means 63. The reduction in size of the heating means 63 is advantageous in that, for example, there is no need to place such a large heater that faces the entire deodorizing means 62 so as to reliably heat the entire deodorizing means 62, thereby simplifying the structure and reducing costs.

Also, with the deodorizer A of this embodiment, the relative positional relationship between the heating means 63 and the deodorizing means 62 is changeable. Thus, for deodorizing the entire deodorizing means 62, the facing part of the deodorizing means 62 and the heating means 63 may be changed, and the heating means 63 does not need to cover the entire deodorizing means 62. Specifically, the deodorizing means 62 may always face the heating means 63 in a limited part, thereby minimizing a region in which the heating means 63 blocks a flow of air flowing through the deodorizing means 62. This allows more air to flow through the deodorizing means 62, and thus allows more odors to be removed from air at one time.

Further, with the deodorizer A of this embodiment, the relative positional relationship between the deodorizing means 62 and the heating means 63 is changeable. Thus, the heating means 63 can reliably face and heat each part of the deodorizing means 62. This can reduce uneven heating between the parts of the deodorizing means 62, and thus can efficiently restore a deodorizing capability of the deodorizing means 62.

Also, with the deodorizer A of this embodiment, the inlet 11 of the deodorizer A is formed in the front surface of the body, and the outlet 42 is formed in any of the side surface, the top surface, or the back surface of the body. With such a configuration, the inlet 11 opening wide easily faces a source of an odor, and thus can suck the odor faster and remove the odor from the indoor air. Also, the outlet 42 is formed in any of the side surface, the top surface, or the back surface of the body, and thus cleaned air is less likely to flow to the source of the odor, thereby preventing spreading of the odor.

Also, with the deodorizer A of this embodiment, the deodorizing means 62 is rotatably supported by the body case C, and the heating means 63 is secured to the body case C closely to the surface of the deodorizing means 62. Thus, the heating means 63 including the heater 63a for generating heat is immovable in the body case C, and there is no need to consider measures for heat in a wide range in the body case C due to wiring for supplying power for heat generation or a position change of the high temperature part in the body case C. Also, since the deodorizing means 62 is rotated to change the surface facing the heating means 63, moving the deodorizing means 62 only in one direction allows the entire surface of the deodorizing means 62 to evenly face the heating means 63.

Also, with the deodorizer A of this embodiment, the deodorizing means 62 is formed into a disk shape, and thus a rotation region of the deodorizing means 62 can be minimized with respect to an area of the deodorizing means 62 seen in the direction of the rotating shaft. Specifically, a placement region of the deodorizing means 62 in the body case C can be reduced.

Also, the deodorizing means 62 is rotated to change the surface facing the heating means 63. Thus, the disk-shaped deodorizing means 62 allows more regions of the deodorizing means 62 to be heated by a heater 63a of the heating means 63 having a size in a diametrical direction of the deodorizing means 62 at least equal to or smaller than a rotation radius of the deodorizing means 62.

Further, the deodorizing means 62 has a disk shape, and thus a larger region can be deodorized with respect to the opening area of the body case C as a rectangular opening while having a configuration that achieves the above described advantage. Thus, more air can flow through the deodorizing means 62, thereby increasing an air volume while maintaining deodorizing power.

Also, with the deodorizer A of this embodiment, the catalyst having functions of adsorbing and oxidatively decomposing an odor of excrement is applied to the surface of the deodorizing means 62 or the surface is impregnated with the catalyst. Thus, the deodorizer can be configured to be capable of heating and thus efficiently oxidatively decomposing odors of pets and odors of nursing in hospitals, nursing homes, nursing sites, or the like with quick deodorization. In particular, the deodorizer of this embodiment can remove odors from more air in a short time, and thus can quickly solve troubles about odors of nursing in places such as hospitals or nursing homes used by many people.

Zeolite has pores in a surface and has a large adsorbing area for a target gas, and thus has a large adsorbing capacity. Thus, zeolite is effective as a medium that is carried by a filter carrier for adsorbing and removing a target gas. Also, heating zeolite does not cause oxidative decomposition of an adsorbed gas, and thus even if alcohol is adsorbed, a sour odor of acetic acid or the like can be prevented from being re-released when the deodorizer is operated. On the other hand, there is zeolite unsuitable for a carrier for adsorbing hydrogen sulfide or a sulfur compound such as methyl mercaptan. Since an odor of excrement contains hydrogen sulfide or a sulfur compound such as methyl mercaptan, an adsorbent for removing a sulfur compound is separately mixed with zeolite in that case.

Zinc oxide has a smaller surface area and has a smaller adsorbing capacity than zeolite, but it is generally known that zinc oxide is effective as an adsorbent for hydrogen sulfide or a sulfur compound such as methyl mercaptan. The zinc oxide has a high adsorbing force, and a sulfur compound is not desorbed in a regeneration process at a rather low temperature of less than 200° C. Thus, zinc oxide is suitable for an adsorbent because a sulfur compound is not re-released during a normal operation of the deodorizer, that is, while air is passed through the deodorizing means 62. This can prevent a foreign odor from being generated by re-releasing of a sulfur compound.

Manganese oxide acts as a catalyst for heating and thus oxidatively decomposing an adsorbed material, and also acts as an adsorbent. Thus, the adsorbed material is oxidatively decomposed into an odorless material, thereby preventing re-releasing of the adsorbed odor when the deodorizer is operated. However, if the reaction is performed at a relatively low temperature range of less than 200° C. as in the embodiment of the present invention, some materials may change into materials having an odor easily perceivable at a lower concentration than that of an original material, and the odor may be re-released when the deodorizer is operated to generate a foreign odor. Thus, a combination amount and a heating time need to be noted.

Also, with the deodorizer A of this embodiment, the blowing fan 44 as the blowing means is located in the air duct R, the deodorizing means 62 is located upstream of the blowing fan 44 in the air duct R, and the heating means 63 is located between the blowing fan 44 and the deodorizing means 62. With such a configuration, a space provided for reducing pressure loss (loss of an air flow) that occurs around the deodorizing means 62 and the fan opening 44*d* of the blowing fan 44 can be used as a space for placing the heating means 63.

Also, with the deodorizer A of this embodiment, the heating means 63 includes the case 63*b* having an opening in the side facing the deodorizing means 62 and having an internal space, and the heater 63*a* that is located in the internal space of the case 63*b* and radiates heat through the opening, and the heater 63*a* has a heating capability of increasing the temperature of the facing part of the deodorizing means 62 to the preset temperature when energized for the preset time. This can remove the odor adsorbed by the deodorizing means 62. The case 63*b* has a fan shape. This can minimize the area covering the deodorizing means 62. The opening angle of the fan shape is formed with reference to a rotation angle of a single motion in rotation of the deodorizing means 62.

Also, with the deodorizer A of this embodiment, the controller 47 includes a control program for driving the driving means 64 as the position changing means at preset timing to rotate the deodorizing means 62. Thus, when the deodorizing means 62 is heated, the controller 47 can cause the part of the deodorizing means 62 to be deodorized to automatically face the heating means 63.

Also, the control program described above has processing steps of driving the driving means 64 at preset timing to rotate the deodorizing means by a preset rotation angle and then stop the deodorizing means, and energize the heating means for a preset time in the stop state. This allows the controller 47 to automatically perform a series of operations from rotation to heating of the deodorizing means 62.

Also, with the deodorizer A of this embodiment, the HEPA filter 12 and the prefilter 13 as dust filtration filters are provided upstream of the deodorizing means 62 in the air duct R, the front panel 10 as an air permeable casing body is detachably mounted to the front surface of the body case C, and with the casing body being removed from the body case C, the dust filtration filter can be taken out forward of the body case C. With such a configuration, the dust filtration filter can be attached or detached from the front side of the body case C, thereby increasing maintenance performance of the dust filtration filter to which large dust tends to adhere.

Also, the air duct R is bent upward on the downstream side of the deodorizing means 62, and the blowing fan 44 is placed in the bent portion. The blowing fan 44 is configured as a multi-blade fan that rotates around the rotating shaft extending horizontally, and feeds air introduced from the front side of the body case C also upward. Such a multi-blade fan (sirocco fan) takes in air in the direction of the rotating shaft of the fan and discharges the taken air radially of the fan. This can provide a linear flow of indoor air from the front surface to the rear of the body case C, and efficiently change the wind direction toward the outlet 42.

Further, with the deodorizer A of this embodiment, the heating means 63 is mounted to the body so as to be located below the rotation center of the deodorizing means 62. As such, the heating means 63 including the heater 63*a* or the like and having a certain weight is placed in a low position to lower the center of gravity of the deodorizer A. Thus, the deodorizer A that can be stably placed on a floor surface can be configured.

Further, with the deodorizer A of this embodiment, the opening 65*a* is located at the middle in the vertical direction of the front of the body case C so that a relationship between the projection area X on front view of the body case C and the area Y of the opening 65*a* on front view is "$Y \geq 0.6X$."

This relationship allows the inlet of the opening 65a to take in maximum indoor air with respect to the area of the body case C on front view, and the deodorizer can be configured capable of taking in more indoor air and passing the air to the deodorizing means 62.

For the deodorizing means 62 in the embodiment, the adsorbent and the catalyst component may be carried by separate carriers on two steps in the air passing direction. In that case, deodorizing means carrying a catalyst component (hereinafter, first deodorizing means) needs to be placed to face the heating means 63, while deodorizing means carrying an adsorbent (hereinafter, second deodorizing means) may not be placed near the heating means 63. However, if the second deodorizing means is not placed near the heating means, that is, the regenerating operation of the deodorizing means carrying the adsorbent is not performed, the second deodorizing means needs to be regularly replaced, and is thus preferably placed in a position where the user can easily replace the second deodorizing means.

The first deodorizing means preferably further carries the adsorbent. When a plurality of components are used as an adsorbent, the components of the same amount may be contained at the same proportion as the adsorbent of the second deodorizing means, or a part of the components may be mixed. In particular, zeolite often has a larger surface area than the catalyst component, and is effective for accumulating odorous components to be oxidatively decomposed. When the catalyst performs an oxidative decomposition reaction, the material adsorbed by the adsorbent is desorbed by heating and reacts with the catalyst to facilitate the oxidative decomposition. Since a reaction speed of the catalyst is also a matter of established contact with the odor material, reaction efficiency increases with increasing concentration around the catalyst. As the adsorbent, an optimum material needs to be selected depending on a required oxidative decomposition ability, a form and a heating temperature of the deodorizing means, presence or absence of an air flow, or the like.

The first deodorizing means carrying the catalyst component is provided separately from the second deodorizing means carrying the adsorbent, thereby allowing an effective deodorization process even in an environment containing a large volume of odors that poisons the catalyst component. In that case, the target odor is previously removed by the second deodorizing means above the first deodorizing means, thereby preventing a foreign odor from being generated during the operation of the deodorizer.

The invention claimed is:

1. A deodorizer comprising:
   a body case having an inlet and an outlet opening outward and an air duct providing communication between the inlet and the outlet;
   a blowing fan included in the body case, for introducing indoor air into the air duct extending from the inlet to the outlet;
   a deodorizing filter provided in a middle of the air duct, introduced air passing through the deodorizing filter;
   a heater placed to face at least a partial region of the deodorizing filter, for heating the deodorizing filter at 200° C. or less;
   a motor for changing position of the deodorizing filter relative to the heater, and
   a controller for controlling operations of the blowing fan and the heater and configured to control an operation of the motor, wherein the controller includes a control program programmed to drive the motor at preset timing to rotate the deodorizing filter;
   the deodorizing filter comprising an adsorbent that does not oxidatively decompose an adsorbed material, a catalyst component that oxidatively decomposes the adsorbed material, and a carrier that carries the adsorbent and the catalyst component;
   the deodorizing filter being configured so that when the deodorizing filter adsorbs ethanol and is heated at a heating temperature of 120° C. to 140° C. for one hour, a rate of conversion into acetic acid representing a ratio of a molar amount of acetic acid released from the deodorizing filter to a molar amount of ethanol having been adsorbed is 15% or less,
   wherein the catalyst component is composed of manganese oxide, and
   wherein in the deodorizing filter, a weight percentage of the manganese oxide with respect to the components carried by the carrier is 5 wt% to 10 wt%.

2. The deodorizer according to claim 1, wherein the adsorbent is composed of hydrophobic zeolite having a silica-alumina ratio of at least 60.

3. The deodorizer according to claim 1, wherein the adsorbent is composed of zinc oxide.

4. The deodorizer according to claim 1, wherein a heating temperature of the heater is set to 120° C. to 140° C.

5. The deodorizer according to claim 1, wherein the heater is not in contact with the deodorizing filter.

6. The deodorizer according to claim 1, wherein the control program includes:
   a processing step of driving the motor at preset timing to rotate the deodorizing filter by a preset rotation angle and then stop the deodorizing filter, and
   a processing step of energizing the heater for a preset time in the stop state.

7. A deodorizer comprising:
   a body case having an inlet and an outlet opening outward, and having an air duct providing communication between the inlet and the outlet;
   a blowing fan included in the body case, for introducing indoor air into the air duct extending from the inlet to the outlet;
   a deodorizing filter provided in a middle of the air duct, introduced air passing through the deodorizing filter;
   a heater placed to face at least a partial region of the deodorizing filter, for heating the deodorizing filter at 200° C. or less;
   a motor for changing position of the deodorizing filter relative to the heater, and
   a controller for controlling operations of the blowing fan and the heater and configured to control an operation of the motor, wherein the controller includes a control program programmed to drive the motor at preset timing to rotate the deodorizing filter;
   the deodorizing filter comprising an adsorbent that does not oxidatively decompose an adsorbed material, a catalyst component that oxidatively decomposes the adsorbed material, and a carrier carrying the adsorbent and the catalyst component, wherein
   the controller is configured to operate the deodorizer in a regenerating operation including heating the deodorizing filter using the heater at a predetermined temperature for a predetermined time, and
   the deodorizing filter is configured to adsorb ethanol and release acetic acid in the regenerating operation, the deodorizing filter containing a weight percentage of the catalyst component with respect to components carried by the carrier being set to provide a rate of conversion of ethanol into acetic acid, that is a ratio of a molar amount of acetic acid released from the deodorizing filter to a molar amount of ethanol having been adsorbed by the catalyst component, of 15% or less on average during the regenerating operation, wherein the catalyst component is composed of manganese oxide, wherein in the deodorizing filter, a weight percentage of the manganese oxide with respect to the components carried by the carrier is 5 wt% to 10 wt%.

8. The deodorizer according to claim 7, wherein the adsorbent is composed of hydrophobic zeolite having a silica-alumina ratio of at least 60.

9. The deodorizer according to claim 7, wherein the adsorbent is composed of zinc oxide.

10. The deodorizer according to claim 7, wherein the heating temperature is set to 120° C. to 140° C., and the heating time is set to one hour.

11. The deodorizer according to claim 7, wherein the heater is not in contact with the deodorizing filter.

12. The deodorizer according to claim 7, wherein the control program includes:

a processing step of driving the motor at preset timing to rotate the deodorizing filter by a preset rotation angle and then stop the deodorizing filter, and a processing step of energizing the heater for a preset time in the stop state.

\* \* \* \* \*